United States Patent
Boese et al.

(10) Patent No.: US 9,153,411 B2
(45) Date of Patent: Oct. 6, 2015

(54) APPARATUS FOR X-RAY IMAGING FOR PROJECTION RADIOGRAPHY AND COMPUTED TOMOGRAPHY, AND METHOD FOR X-RAY IMAGING

(75) Inventors: Jan Boese, Eckental (DE); Frank Dennerlein, Forchheim (DE); Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 473 days.

(21) Appl. No.: 13/564,909

(22) Filed: Aug. 2, 2012

(65) Prior Publication Data

US 2013/0034201 A1  Feb. 7, 2013

(30) Foreign Application Priority Data

Aug. 2, 2011 (DE) .......................... 10 2011 080 263

(51) Int. Cl.
| | |
|---|---|
| *H01J 35/00* | (2006.01) |
| *H01J 35/30* | (2006.01) |
| *A61B 6/03* | (2006.01) |
| *A61B 6/00* | (2006.01) |

(52) U.S. Cl.
CPC . *H01J 35/30* (2013.01); *A61B 6/03* (2013.01); *A61B 6/4435* (2013.01)

(58) Field of Classification Search
USPC ............................................................ 378/9
See application file for complete search history.

(56) References Cited

U.S. PATENT DOCUMENTS

| | | | | |
|---|---|---|---|---|
| 4,812,983 | A * | 3/1989 | Gullberg et al. | 378/14 |
| 6,198,790 | B1 | 3/2001 | Pflaum | |
| 6,980,623 | B2 * | 12/2005 | Dunham et al. | 378/19 |
| 7,342,992 | B2 * | 3/2008 | Schomberg | 378/19 |
| 7,769,129 | B2 * | 8/2010 | Hein et al. | 378/19 |
| 8,208,600 | B2 * | 6/2012 | Tsumuraya et al. | 378/9 |
| 2007/0025498 | A1 * | 2/2007 | Matsuda | 378/9 |
| 2010/0020918 | A1 | 1/2010 | Popescu et al. | |
| 2010/0054395 | A1 | 3/2010 | Noshi et al. | |

FOREIGN PATENT DOCUMENTS

| | | |
|---|---|---|
| DE | 198 02 405 A1 | 8/1999 |
| DE | 102008034584 A1 | 2/2010 |

* cited by examiner

*Primary Examiner* — Phillip A Johnston
(74) *Attorney, Agent, or Firm* — Laurence A. Greenberg; Werner H. Stemer; Ralph E. Locher

(57) ABSTRACT

An X-ray imaging apparatus has at least one X-ray image system rotatable about an examination volume. The X-ray image system is controlled such that during a continuous rotation of the system, at least one 2D projection image is recorded. An image generation facility generates the 2D projection image from the measured data. The X-ray source includes an X-ray focus which can be changed in terms of position, which, during the recording of the 2D projection image, moves counter to the direction of rotation of the X-ray image system such that its spatial position in a fixed coordinate system does not change. The X-ray detector records several 2D partial images, from which the 2D projection image is calculated with the rotational movement of the X-ray detector being at least approximately compensated. The 2D projection images have significantly reduced image blur.

14 Claims, 5 Drawing Sheets

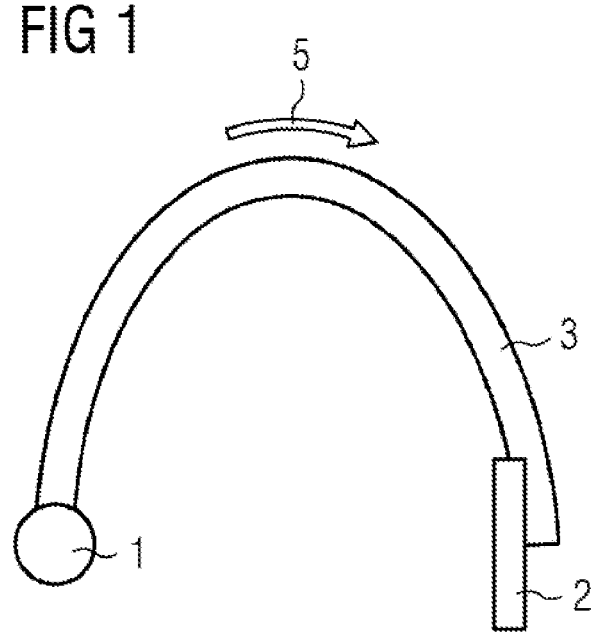
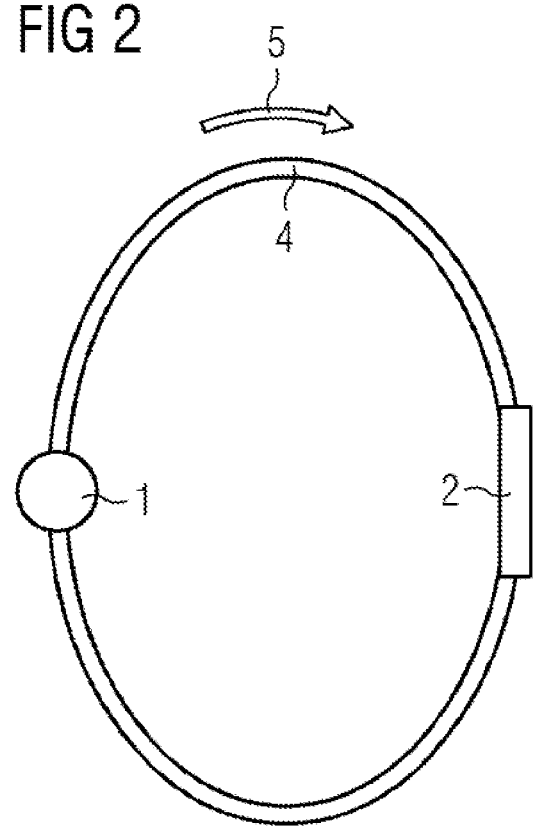

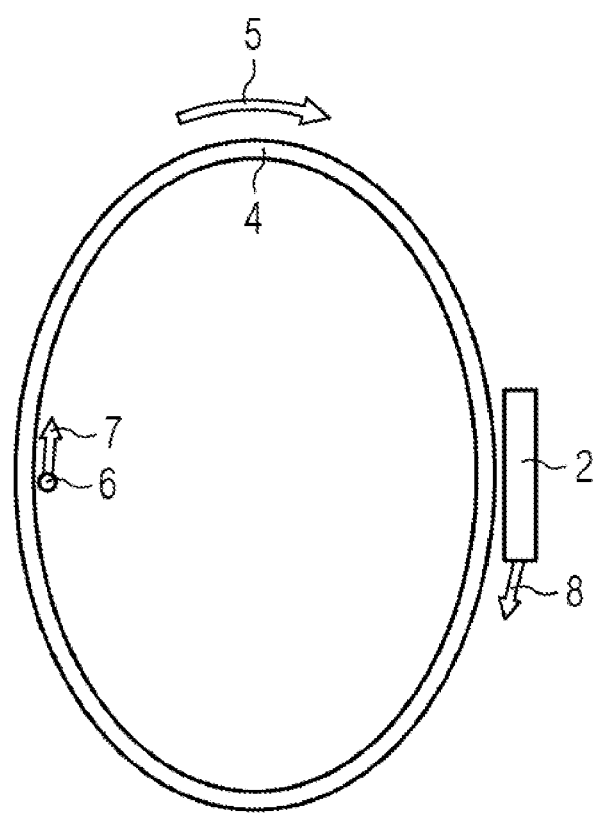

APPARATUS FOR X-RAY IMAGING FOR PROJECTION RADIOGRAPHY AND COMPUTED TOMOGRAPHY, AND METHOD FOR X-RAY IMAGING

CROSS-REFERENCE TO RELATED APPLICATION

This application claims the priority, under 35 U.S.C. §119, of German patent application DE 10 2011 080 263.0, filed Aug. 2, 2011; the prior application is herewith incorporated by reference in its entirety.

BACKGROUND OF THE INVENTION

Field of the Invention

The present invention relates to an apparatus for X-ray imaging having at least one X-ray image system which can be rotated about an examination volume. The X-ray image system comprises an X-ray source with an X-ray focus and an X-ray detector disposed opposite the X-ray source having several rows and columns of detector elements, a control facility which controls the X-ray image system in an operating mode of the apparatus such that during a continuous rotation of the X-ray image system, at least one 2D projection image of an object disposed in the examination volume is recorded and an image generation facility, which can generate the 2D projection image from measured data of the X-ray detector. The invention also relates to a correspondingly embodied method for X-ray imaging.

With apparatuses for X-ray imaging, both high resolution 2D projection views and also 3D representations of the inner structures of an object can be obtained. With some applications, it is desirable to generate both one or several 2D projection images and also 3D tomography images at the same time or at short intervals using the same device. Commonly assigned U.S. Pat. No. 6,198,790 B1 and its counterpart German patent application DE 198 02 405 A1 describe a computed tomography system embodied herefor, comprising two separate X-ray image systems on the rotating frame. The first X-ray image system with an X-ray tube and a flat panel detector with several rows and columns of detector elements and/or pixels is used to record a 2D projection image. The second X-ray image system is embodied to record 3D tomography images. Simultaneous operation of both X-ray image systems allows 2D projection images to be repeatedly recorded during the recording of the 3D tomography image.

A sufficiently high radiation dose is needed to record a 2D projection image with high image quality, in particular a high signal-to-noise ratio. The exposure time for the image capture is therefore not permitted to be selected too short. The pulse duration and/or exposure time for a 2D image capture of this type in fluoroscopy mode usually lies between 4 and 10 ms. With the afore-cited hybrid system having the two separate X-ray image systems for tomography and projection images, the rotating frames rotate with the X-ray image systems during recording of the 2D projection image. With a typical rotational speed of the rotating frame of one rotation per second about the object to be imaged, the flat panel detector covers approximately 13-31 mm per pulse duration, i.e. per exposure (at a distance of 1000 mm between the X-ray source and X-ray detector). In the 2D projection image, this results in a motion blur and thus in turn in reduced image quality.

In order to avoid this problem, the rotational speed of the rotating frame is currently reduced during the image recording of the 2D projection image or alternatively the rotating frame is completely stopped. Nevertheless, changes in the speed of the rotating frame are then frequently needed to record several 2D projection images, which involves significant time and energy.

SUMMARY OF THE INVENTION

It is accordingly an object of the invention to provide an apparatus and a method for X-ray imaging which overcome the above-mentioned disadvantages of the heretofore-known devices and methods of this general type and which provides for specifying X-ray imaging, with which 2D projection images with a high image quality can be recorded during a continuous rotation of the X-ray image system about the examination volume without reducing the rotational speed during the image capture. The apparatus and the method are in this way to enable above all simultaneous recording of 3D tomography and 2D projection images in a hybrid system which has two separate X-ray image systems for the two image types.

With the foregoing and other objects in view there is provided, in accordance with the invention, an apparatus for X-ray imaging, comprising:

an X-ray image system rotatably disposed about an examination volume, the X-ray image system including an X-ray source and an X-ray detector facing toward the X-ray source and having rows and columns of detector elements;

a control facility configured to control the X-ray image system in a given operating mode of the apparatus to record at least one 2D projection image of an object located in the examination volume during a continuous rotation of the X-ray image system;

an image generation facility connected to receive measured data from the X-ray detector and configured to generate the 2D projection image from the measured data of the X-ray detector;

the X-ray source including an X-ray focus that can be changed in position which, during a recording of the 2D projection image, moves counter to a direction of rotation of the X-ray source so that a spatial position thereof does not change in a fixed coordinate system, or at least to a lesser degree than a position of the X-ray source;

the control facility controlling the X-ray image system in the given operating mode to record the 2D projection image by consecutively recording several 2D partial images, and the image generation facility calculating from the several 2D partial images the 2D projection image to at least substantially compensate for the rotation movement of the X-ray detector during the recording of the 2D partial images.

In other words, the invention relates in a preferred embodiment to a hybrid system having at least two separate X-ray image systems, a first X-ray image system of which is embodied to record 2D projection images and the second X-ray image system of which is embodied to record 3D tomography images. In a simplified embodiment, the proposed apparatus can nevertheless also comprise just one single X-ray image system, with which both 2D projection images and also 3D tomography images can be recorded. The image capture then takes place sequentially so that the image capture of the 3D tomography images is briefly interrupted for the image capture of a 2D projection image, without nevertheless changing the rotational speed of the two X-ray image systems.

The proposed apparatus accordingly includes at least one X-ray image system which can be rotated about an examination volume, the X-ray image system comprising an X-ray source with an X-ray focus and an X-ray detector facing the X-ray source, the X-ray detector preferably being embodied as a flat panel detector. The X-ray detector has a number of rows and columns of detector elements and/or pixels, which are sufficient to record 2D projection and/or 2 D fluoroscopy images. The apparatus includes a control facility, which controls this X-ray image system in an operating mode of the apparatus such that during a continuous rotation of the X-ray image system and the examination volume, at least one 2D projection image of an object arranged in the examination volume is recorded. In an image generation facility, the measured values and/or measured data supplied by the X-ray detector are processed in order to generate the 2D projection image. The correspondingly generated image is then stored on a storage medium and/or displayed on a monitor. The proposed apparatus is characterized in that an X-ray source with an X-ray focus which can be changed in the position within the X-ray source is used, which, during the capture of the 2D projection image, moves counter to the direction of rotation of the X-ray source such that its spatial position in a fixed coordinate system does not change or only changes to a minimal degree as without this movement within the X-ray source. The X-ray source is to this end controlled accordingly by the control facility. Furthermore, several 2D partial images are recorded one after the other by the X-ray detector in order to record the 2D projection image, from which 2D partial images the image generation facility then calculates the 2D projection image. A 2D partial image is herewith understood to mean a complete 2D projection image, which is only recorded with a shorter exposure time than the final 2D projection image should have, which is calculated from these partial images. The calculation takes place here such that the rotational movement of the X-ray detector is at least approximately compensated for during the recording of 2D partial images. The individual 2D partial images are to this end moved counter to one another during calculation according to the rotational movement of the X-ray detector having taken place herebetween in order in each instance to overlay the image data of the same structures of the imaged object when calculating the 2D projection image. Suitable summing or averaging of the individual images then produces the 2D projection and/or fluorescence image.

With the proposed apparatus and the associated method, the very precisely known movement and/or rotation of the X-ray image system about the examination volume during the image capture of the 2D projection image and/or the 2D partial images are at least partially compensated for by a non-mechanical balancing movement in order to prevent motion blurs. This balancing movement must include both the X-ray focus and also the X-ray detector. With the X-ray focus, this is achieved by using an X-ray source, in which the position of the X-ray focus in the X-ray source can be moved by a suitable controller. X-ray sources of this type are known from other applications, for instance from the field of diagnostic computed tomography (flying focal spot method). With the proposed apparatus and associated method, the X-ray focus is moved here during the image capture of the 2D projection image counter to the direction of rotation of the X-ray source such that it is preferably static when the coordinate system of the apparatus is fixed during image capture.

In an advantageous embodiment, an X-ray tube is used, in which the X-ray focus and/or X-ray focal spot is generated by accelerating an electron beam onto an X-ray target. By electronically deflecting the electron beam, the position of the X-ray focus on the target can then be changed. The electronic diversion and/or deflection can take place very quickly and be controlled precisely.

The balancing of the movement of the X-ray detector takes place in a calculational fashion, by the several 2D partial images recorded one after the other during the rotational movement being suitably moved counter to one another in the direction of rotation and then being calculated with one another. This can take place in one embodiment with an image-based method, with which the individual images are registered with one another so that the individual pixels of each image are assigned to one another, which indicate the same position of the examination object. The intensities of the respectively assigned pixels are then summed or averaged in a suitable fashion in order to achieve the final 2D projection image. Suitable methods for image-based registration of digital images are known to the person skilled in the art.

In another embodiment, the knowledge of the rotational movement of the X-ray detector is used in order to suitably displace the individual images counter to one another prior to calculation i.e. summing or averaging pixel by pixel, and as a result to compensate for the rotational movement between the individual images.

In an advantageous embodiment of the proposed apparatus, a second X-ray image system having an X-ray source and an X-ray detector disposed opposite the X-ray source is available in addition to the X-ray image system for recording the 2D projection images, said second X-ray detector being embodied to record 3D tomography images. The X-ray detector may herewith comprise a lower number of rows and/or columns than the X-ray detector of the other X-ray image system. The control facility and the image evaluation facility are in this case then embodied similarly in order to control the image recording of a 3D tomography image and/or to generate a 3D tomography image from the measured data or measured values of the X-ray detector of this second X-ray image system. The two X-ray image systems are preferably arranged offset counter to one another in the direction of rotation, for instance in order to offset an angle of 90°. A hybrid system of that type is known for instance from the above-mentioned U.S. Pat. No. 6,198,790 B1 and DE 198 02 405 A1.

The control facility is preferably embodied in this embodiment such that during the image recording of a 3D tomography image by the second X-ray image system, the first X-ray image system is repeatedly controlled for simultaneous recording of a 2D projection image. A change in the rotational speed of the two X-ray image systems about the examination volume is not necessary here. Similarly, the image recording of the 3D tomography image must not be interrupted during the image recording of the 2D projection image. The apparatus consequently enables high quality 2D projection imaging even during a rapid movement of the X-ray image recording systems, since the compensation measures shown reduce or balance out the movement of the X-ray focus and of the X-ray detector during the exposure. This relates in particular to the compensation movement of the X-ray focus and/or X-ray focal spot and the multiple recordings of the X-ray detector during the exposure and/or X-ray pulse duration for recording the 2D projection image.

The proposed apparatus can be embodied as a computed tomograph for instance, wherein the first and if necessary second X-ray image system are then arranged in a known manner on the rotational frame of the computed tomography system. The apparatus can also be embodied as a C-arm device, wherein the first and if necessary second X-ray image system are then fastened on the C-arm of this device.

With the above and other objects in view there is also provided, in accordance with the invention, an X-ray imaging method, performed with at least one X-ray image system that is rotatable about an examination volume and that includes an X-ray source with an X-ray focus and an X-ray detector facing the X-ray source, wherein the X-ray detector has a plurality of rows and columns of detector elements. The imaging method comprises:

continuously rotating the X-ray image system and thereby recording at least one 2D projection image of an object located in the examination volume;

moving the X-ray focus during the recording of the 2D projection image counter to a direction of rotation of the X-ray source so that spatial position thereof in a fixed coordinate system is not changed or changed to a lesser degree that the position of the X-ray source;

recording the 2D projection image by recording several 2D partial images one after the other, and calculating the 2D projection image from the 2D partial images such that the rotational movement of the X-ray detector during the recording of the 2D partial images is at least substantially compensated.

In other words, in the novel method, at least one 2D projection image is therefore recorded using an X-ray image system which can be rotated about an examination volume during the continuous rotation of the X-ray image system. During this recording, the X-ray focus of the used X-ray source is moved counter to the direction of rotation in the X-ray source such that its spatial position in the fixed coordinate system of the apparatus is preferably fixed and/or static. A higher image quality is already achieved than without this partial compensation movement even with a movement in the fixed coordinate system of the apparatus which is only reduced compared with the rotational movement. At the same time, several 2D partial images are recorded one after the other with the X-ray detector during the image recording and/or exposure, said 2D partial images then being moved counter to one another and calculated with one another such that a 2D projection image is obtained, with which the rotational movement is at least approximately compensated for during the recording time.

Other features which are considered as characteristic for the invention are set forth in the appended claims.

Although the invention is illustrated and described herein as embodied in an apparatus for X-ray imaging for projection radiography and computed tomography as well as a correspondingly embodied method for X-ray imaging, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 1 shows a schematic representation of the arrangement of X-ray source and X-ray detector in a C-arm device;

FIG. 2 shows a schematic representation of the arrangement of X-ray source and X-ray detector in a computer tomography system;

FIG. 3 shows a representation to clarify the movement of the X-ray source and X-ray detector during a rotation of the rotational frame in a computed tomography system;

DETAILED DESCRIPTION OF THE INVENTION

Figure 4:
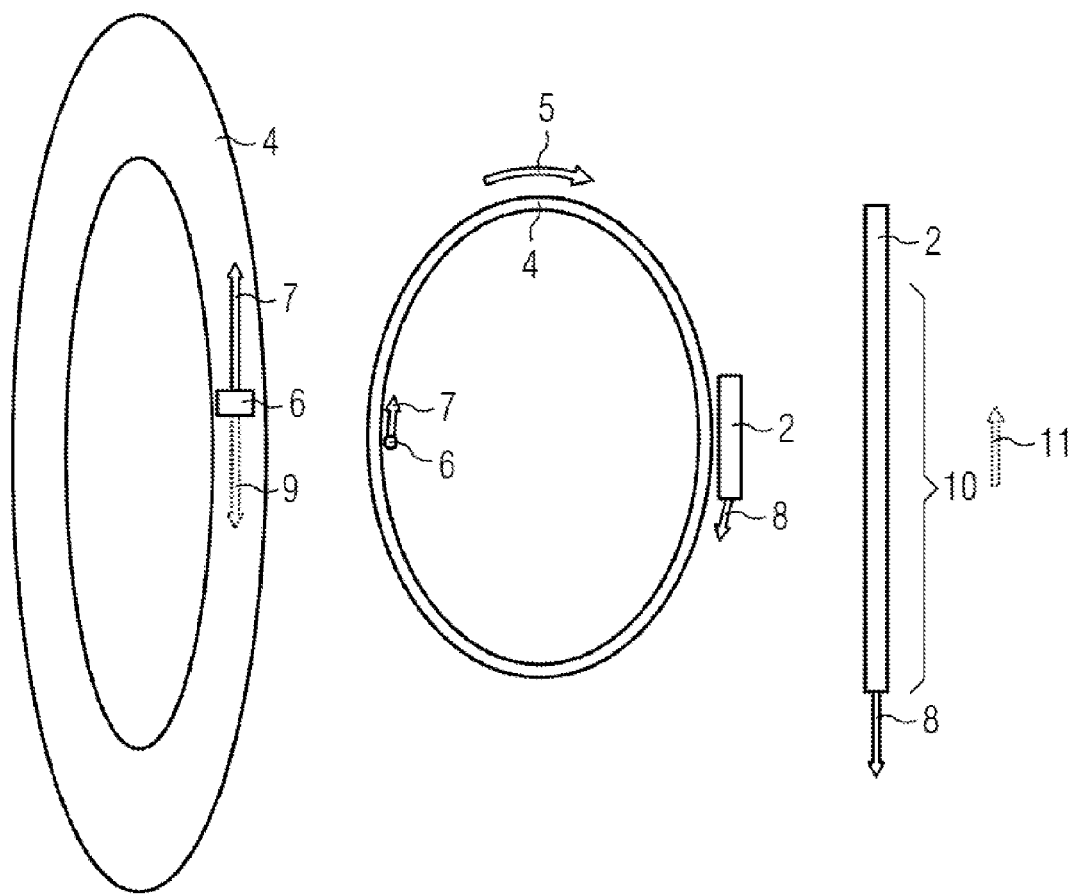
FIG. 4 shows a representation of the compensation movement of the X-ray focus and an effective detector surface of the X-ray detector according to the present invention.

The effect of the present invention is based on it being possible to avoid motion blurs in the image recording of a static object if the recording geometry does not change during the exposure. In the event of recording a 2D projection image, the spatial coordinates of the X-ray focus and/or X-ray focal spot and the detector elements used for the recording are therefore not to change during the exposure or X-ray pulse duration indicating this exposure. The rotational movement of the X-ray image system nevertheless previously produced a change in the recording geometry of this type. This relates both to X-ray C-arm devices, in which the X-ray tube 1 and the X-ray detector 2 are fastened on the C-arm 3 of the X-ray device, and also computed tomography systems (CT), in which X-ray tube 1 and X-ray detector 2 are arranged on the rotational frame 4. In both cases, a rotation 5 of the C-arm 3 and/or of the rotational frame 4, as indicated in FIGS. 1 and 2, takes place during the recording of 3D tomography images. If a 2D projection image is to be recorded during this rotation, the recording geometry changes during the exposure, so that the unwanted motion blur is generated. FIG. 3 to this end once again shows the movement 7 of the focal spot 6 and the movement 8 of the detector 2 during a recording of a 2D projection image in the example of a computed tomography system.

In the present example, the movement of the recording geometry is compensated for by a non-mechanical balancing movement on account of the known mechanical system movement during the exposure. This balancing movement includes both the X-ray source and also the X-ray detector and is described again in more detail below with reference to FIG. 4. This figure shows in turn, in different views, the rotational movement 5 of the rotational frame 4 of a computed tomography system during an exposure for recording a 2D projection image and the movements 7, 8 of the focal spot 6 and the detector 2 resulting therefrom. The mechanical movement of the X-ray source and thus of the X-ray focal spot 6 is compensated for in this example by an electronic deflection of the X-ray focal spot 6 in the opposite direction. In this process the focal spot 6 moves during the exposure in the X-ray tube about the same distance counter to the direction of rotation, in order to move the X-ray tube in the direction of rotation during this time. This is indicated in the Fig. with a focal spot movement 9 shown with a dashed line. The electronic deflection of the focal spot 6 can take place with the same techniques as are used for instance in diagnostic CT for flying focal spot methods. The electronic deflection can take place very rapidly and be controlled precisely. During the exposure time and/or pulse duration of the X-ray radiation, the position of the focal spot 6 is in this way deflected linearly in the tangential direction, wherein the speed of the focal spot movement is precisely counter to the path speed of the rotational frame. In this way the X-ray focus in the fixed coordinate system remains static during the exposure duration for recording the 2D projection image.

In order to balance out the detector movement, a computational method is used, which is based on recording several projection partial images during the exposure phase and then averaging the same in order to generate the desired 2D projection image. Prior to this averaging, a registration of the individual partial images nevertheless takes place with an image-based method and/or by using the known movement of the rotational frame. This is indicated to the right in FIG. 3. In the simplest case, the images are herewith displaced, prior to averaging, counter to one another in the tangential direction by a value, which results from the path covered by the detector 2 during the pulse duration and/or exposure time divided by the number of partial images. A correspondingly reduced, effective detector surface 10 is obtained in this way, wherein the partial image pixels which contribute to the overall image, are approximately static in the fixed coordinate system. The resulting compensation movement 11 of the effective detector zone 10 during a recording of a 2D projection image is shown schematically in FIG. 4.

Figure 5:
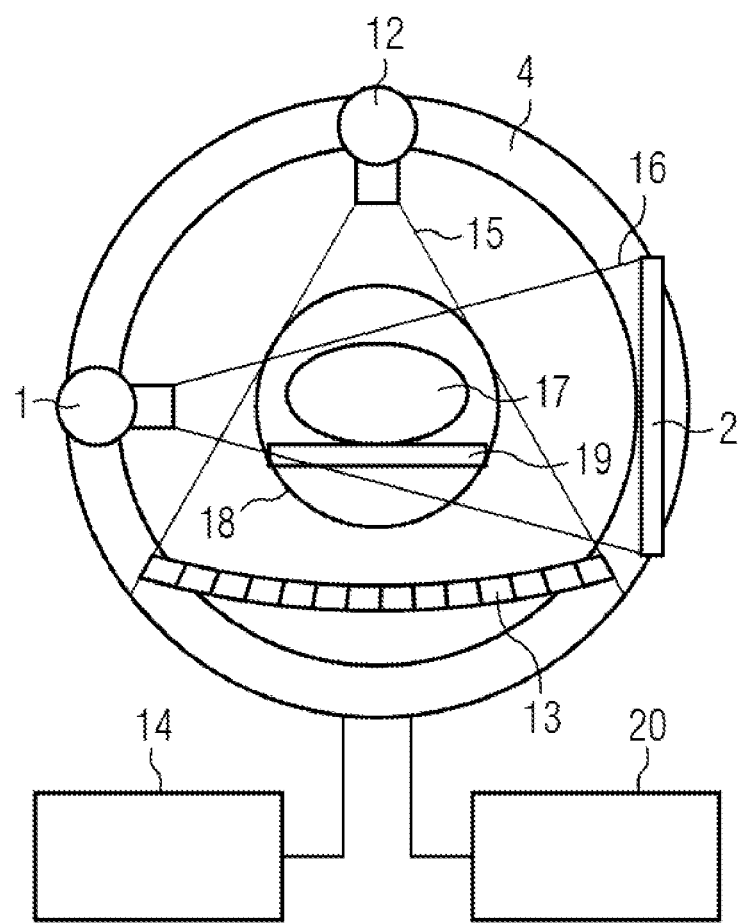
FIG. 5 shows an example of a hybrid system, which is embodied according to the present invention.

FIG. 5 shows a highly schematic example of a hybrid system, in which two separate X-ray image systems are used in a computed tomography system. Both X-ray image systems consist in each instance of an X-ray tube 1, 12, and an X-ray detector 2, 13, each of which is fastened on the rotational frame 4 of the computed tomography system. The first X-ray image system with X-ray tube 1 and X-ray detector 2 is embodied to record 2D projection images, whereas the second X-ray image system 12, 13 is optimized to record 3D tomography images. A control facility 14 controls the computed tomography system and the two X-ray image systems such that during the rotation of the rotational frame 4 with the second X-ray image system, 3D tomography images are recorded, while at the same time being made into 2D projection recordings at different times with the first X-ray image system. In this process the X-ray tubes 1, 12 X-ray an object 17 with their X-ray beam bundles 15, 16, said object 17 being disposed in the examination region 18 on a patient support couch 19. The measured values and/or measured data of the two X-ray detectors 2, 13 are processed by the image evaluation facility 20 in order to generate the corresponding 3D tomography images and 2D projection images and to display the same on a monitor (not shown in the figure).

Figure 6:
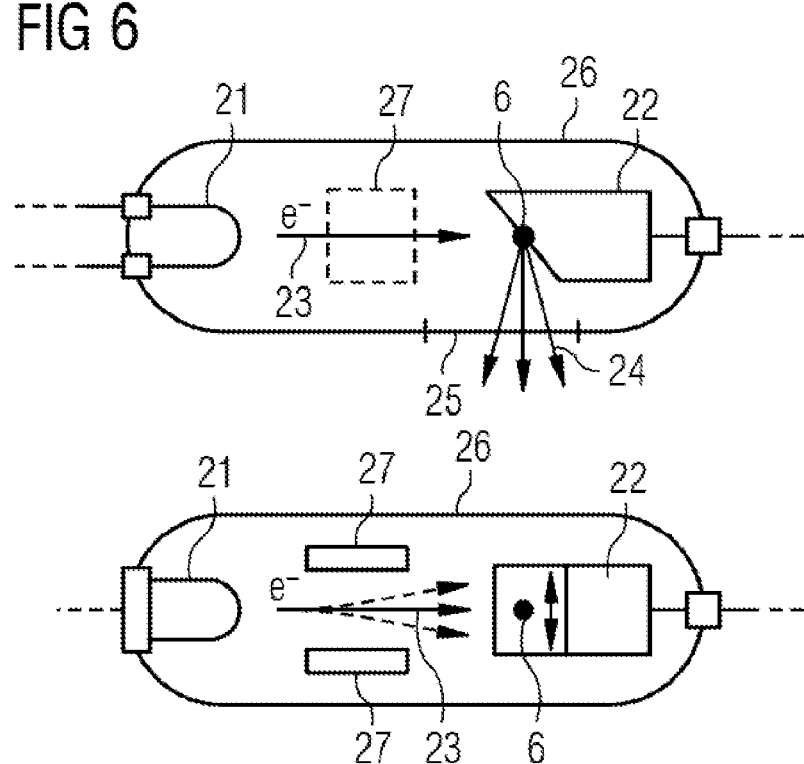
FIG. 6 shows a side view and top view of a schematic representation of an X-ray tube having a deflection facility for moving the X-ray focus.

FIG. 6 shows a highly schematic structure of an X-ray tube having hot cathode 21 and the anode 22 forming the target. The electrons are emitted by the hot cathode 21 and accelerated onto the target as an electron beam 23, in order there to generate the X-ray radiation 24, which leaves via a window 25 in the X-ray tube 26. Additional deflection coils 27 are provided in the proposed X-ray tube, which can deflect the electron beam 23 in the side view of the X-ray tube 26 in the direction at right angles to the plane. This is again more easily visible in the top view onto the X-ray tube 26, which shows the deflection of the electron beam 23 and thus of the generated X-ray focal spot 6 on the anode 22.

Figure 7:
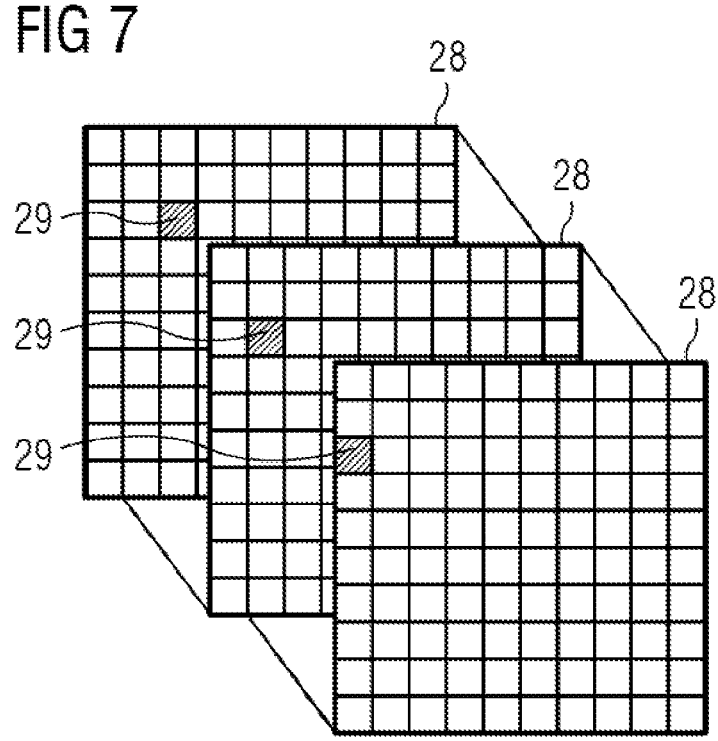
FIG. 7 shows an example for generating a 2D projection image from individual images.

FIG. 7 finally shows again an example of three partial images 28, which were recorded in temporal sequence with the X-ray detector during the rotational movement. The individual pixels are indicated in the Fig. by the square in the partial images 28. The movement of the X-ray detector during the exposure moves a structure 29 of the object in this example in each instance about a pixel from image to image. Correspondingly displaced overlay of partial images 28, as indicated in the Figure, compensate for this on account of the displacement containing the movement. A 2D projection image with a correspondingly reduced motion blur is then generated by averaging across the pixels arranged one above the other in each instance on the images overlayed in this way.

Although the invention was illustrated and described in more detail by means of the exemplary embodiments, the invention is not restricted by the disclosed examples and other variations can be derived by the person skilled in the art without departing from the protective scope of the invention. In one embodiment of the proposed apparatus having two X-ray image recording systems, these X-ray image recording systems can also be offset at an angle relative to one another on the rotational frame or on a C-arm, as shown in FIG. 5.

The invention claimed is:

1. An apparatus for X-ray imaging, comprising:
an X-ray image system rotatably disposed about an examination volume, said X-ray image system including an X-ray source and an X-ray detector facing toward said X-ray source and having rows and columns of detector elements;
a control facility configured to control said X-ray image system in a given operating mode of the apparatus to record at least one 2D projection image of an object located in the examination volume during a continuous rotation of said X-ray image system;
an image generation facility connected to receive measured data from said X-ray detector and configured to generate the 2D projection image from the measured data of said X-ray detector;
said X-ray source including an X-ray focus that can be changed in position wherein, during a recording of the 2D projection image, a speed in which the position of the X-ray focus is changed is precisely counter to a path speed of rotation of said X-ray source so that a spatial position of said X-ray focus does not change in a fixed coordinate system, or at least to a lesser degree than a position of said X-ray source;
said control facility controlling said X-ray image system in the given operating mode to record the 2D projection image by consecutively recording several 2D partial images, and said image generation facility calculating from the several 2D partial images the 2D projection image to at least substantially compensate for the rotation movement of said X-ray detector during the recording of the 2D partial images.

2. The apparatus according to claim 1, wherein said X-ray image system is a first X-ray image system and the apparatus further comprises a second X-ray image system rotatably disposed about the examination volume, and wherein said control facility and said image generation facility are configured to record a 3D tomography image of the object with said second X-ray image system.

3. The apparatus according to claim 2, wherein said control facility controls said first and second X-ray image systems in the given operating mode of the apparatus such that the recording of a 2D projection image takes place once or several times during the recording of the 3D tomography image.

4. The apparatus according to claim 1, wherein a movement of said X-ray focus is effected by electronically deflecting an electron beam that is directed at a target of said X-ray source in order to generate the X-ray focus.

5. The apparatus according to claim 1, wherein said image generation facility is configured to execute a calculation of the 2D projection image from the 2D partial images by image-based registration and subsequent calculation of the 2D partial images.

6. The apparatus according to claim 1, wherein said image generation facility is configured to execute a calculation of the 2D projection image by mutual displacement of the 2D partial images about individual pixels according to the rotational movement and subsequent calculation of the 2D partial images.

7. The apparatus according to claim 1, configured as a computed tomography system having said X-ray image system mounted to a rotational frame.

8. The apparatus according to claim 2, configured as a computed tomography system having said first and second X-ray image systems mounted to a rotational frame.

9. The apparatus according to claim 1, which comprises a C-arm having said X-ray image system fastened thereto, embodying the apparatus as a C-arm device.

10. An X-ray imaging method, comprising:
providing at least one X-ray image system that is rotatable about an examination volume and includes an X-ray source with an X-ray focus and an X-ray detector facing the X-ray source, the X-ray detector having a plurality of rows and columns of detector elements;
continuously rotating the X-ray image system and thereby recording at least one 2D projection image of an object located in the examination volume;
moving the X-ray focus during the recording of the 2D projection image at a speed precisely counter to a path speed of rotation of the X-ray source so that spatial position of said X-ray focus in a fixed coordinate system is not changed or changed to a lesser degree than the position of the X-ray source;
recording the 2D projection image by recording several 2D partial images one after the other, and calculating the 2D projection image from the 2D partial images such that the rotational movement of the X-ray detector during the recording of the 2D partial images is at least substantially compensated.

11. The method according to claim 10, which comprises providing an X-ray imaging apparatus with a second X-ray image system which can be rotated about the examination volume, and recording with the second X-ray image system a 3D tomography image of the object, wherein the recording of the 2D projection image takes place one or several times during the recording of the 3D tomography image.

12. The method according to claim 10, wherein the step of calculating the 2D projection image from the 2D partial images comprises carrying out image-based registration and subsequent calculation of the 2D partial images.

13. The method according to claim 10, wherein the step of calculating the 2D projection image comprises mutual displacement of the 2D partial images about individual pixels according to the rotational movement and subsequent calculation of the 2D partial images.

14. An apparatus for X-ray imaging, comprising:
an X-ray image system rotatably disposed about an examination volume, said X-ray image system including an X-ray source and an X-ray detector facing toward said X-ray source and having rows and columns of detector elements;
a control facility configured to control said X-ray image system in a given operating mode of the apparatus to record at least one 2D projection image of an object located in the examination volume during a continuous rotation of said X-ray image system;
an image generation facility connected to receive measured data from said X-ray detector and configured to generate the 2D projection image from the measured data of said X-ray detector;
said X-ray source including an X-ray focus that can be changed in position wherein, during a recording of the 2D projection image, a speed in which the position of the X-ray focus is changed is precisely counter to a path speed of rotation of said X-ray source so that a spatial position of said X-ray focus does not change in a fixed coordinate system, or at least to a lesser degree than a position of said X-ray source, said X-ray image system configured to deflect said X-ray focus during the recording of the 2D projection image linearly in the tangential direction at a speed precisely counter to the path speed of the X-ray source;
said control facility controlling said X-ray image system in the given operating mode to record the 2D projection image by consecutively recording several 2D partial images, and said image generation facility calculating from the several 2D partial images the 2D projection image to at least substantially compensate for the rotation movement of said X-ray detector during the recording of the 2D partial images.

* * * * *